United States Patent [19]

Brewer et al.

[11] 4,004,018
[45] Jan. 18, 1977

[54] 2,3-DIHYDRO-1,4-DITHIIN 1,1,4,4-TETROXIDE ANTIMICROBIALS

[75] Inventors: Arthur D. Brewer, Puslinch, Canada; Robert A. Davis, Cheshire, Conn.

[73] Assignees: Uniroyal, Inc., New York, N.Y.; Uniroyal, Ltd., Montreal, Canada

[22] Filed: June 20, 1974

[21] Appl. No.: 481,010

[52] U.S. Cl. .............................. 424/277; 260/327 P
[51] Int. Cl.² .................. A01N 9/14; C07D 339/08
[58] Field of Search ................ 260/327 P; 424/277

[56] References Cited

UNITED STATES PATENTS

| | | | |
|---|---|---|---|
| 3,439,051 | 4/1969 | Levine | 260/652 R |
| 3,755,362 | 8/1973 | Asinger et al. | 260/327 P |

FOREIGN PATENTS OR APPLICATIONS

| | | | |
|---|---|---|---|
| 1,957,860 | 5/1971 | Germany | 260/327 P |

OTHER PUBLICATIONS

Levine, "American Chemical Society Abstracts of Papers," (1968), 155th Meeting, p. 24.

Friedman et al., "J. Org. Chem.," vol. 37 (1972), p. 1902.

*Primary Examiner*—Henry R. Jiles
*Assistant Examiner*—R. W. Ramsuer
*Attorney, Agent, or Firm*—James J. Long

[57] ABSTRACT

Fungi, bacteria and viruses are controlled, especially on plants, by application of chemicals of the formula:

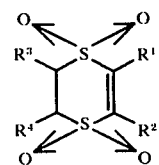

such as 2,3-dihydro-5-phenyl-1,4-dithiin 1,1,4,4-tetroxide, 2-ethyl-5,6-dihydro-3-methyl-1,4-dithiin 1,1,4,4-tetroxide and 2,3-dihydro-5-methyl-2-phenyl-1,4-dithiin 1,1,4,4-tetroxide.

35 Claims, No Drawings

2,3-DIHYDRO-1,4-DITHIIN 1,1,4,4-TETROXIDE ANTIMICROBIALS

This invention relates to a method of controlling microorganisms, to antimicrobial compositions useful in such method, and to new chemical compounds.

Copending application Ser. No. 357,757, filed May 7, 1973, of Arthur D. Brewer, Robert W. Neidermyer and William S. McIntire, now U.S. Pat. No. 3,920,438, issued Nov. 18, 1975, the disclosure of which is hereby incorporated herein by reference, teaches substituted dithiin tetroxide plant growth regulants, certain of which are useful in the present invention.

The invention involves applying to a locus, subject to attack by microorganisms, a 2,3-dihydro-1,4-dithiin 1,1,4,4-tetroxide of the formula

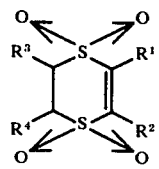

wherein $R_1$, $R_2$, $R_3$ and $R_4$ are typically selected from the group consisting of hydrogen, alkyl having 1 to 14 carbon atoms, aryl (especially phenyl or naphthyl), aryl substituted with one to three substituents selected from lower alkyl (e.g., methyl, ethyl, propyl, butyl), halogen (e.g., chlorine, bromine, fluorine), lower alkoxy (e.g., methoxy, ethoxy, propoxy, butoxy), nitro, and aryl (e.g., phenyl), alkoxymethyl wherein the alkyl group contains 1 to 8 carbon atoms, aryloxymethyl (e.g., phenoxymethyl), alkylaminomethyl wherein the alkyl groups contains 1 to 8 carbon atoms, or adjacent R's may be joined together in the form of a chain of 3 to 4 methylene groups.

The invention is particularly concerned with the control of such microorganisms as fungi, bacteria, and viruses (especially on plant life), by application of a composition containing a 2,3-dihydro-1,4-dithiin 1,1,4,4-tetroxide of a stated formula in amount effective to control the fungi, bacteria or viruses, in admixture with a carrier for the 2,3-dihydro-1,4-dithiin 1,1,4,4-tetroxide, wherein the R's have sets of values as shown in TABLE I.

TABLE I

Antimicrobial Compounds

| $R_1$ | $R_2$ | $R_3$ | $R_4$ |
|---|---|---|---|
| H | H | H | H |
| $CH_3$ | H | H | H |
| $CH_3$ | H | $CH_3$ | H |
| $CH_3$ | H | H | $CH_3$ |
| $CH_3$ | $CH_3$ | $nC_6H_{13}$ | H |
| $CH_3$ | H | $C_2H_5$ | H |
| $CH_3$ | H | H | $C_2H_5$ |
| $CH_3$ | $CH_3$ | $nC_8H_{17}$ | H |
| $CH_3$ | H | $C_6H_5$ | H |
| $CH_3$ | H | H | $C_6H_5$ |
| $CH_3$ | H | $nC_8H_{17}$ | H |
| $CH_3$ | H | H | $nC_8H_{17}$ |
| $CH_3$ | H | $CH_3$ | $CH_3$ |
| $CH_3$ | $CH_3$ | $CH_3$ | $CH_3$ |
| $C_2H_5$ | H | H | H |
| $C_2H_5$ | H | $CH_3$ | H |
| $C_2H_5$ | H | H | $CH_3$ |
| $C_2H_5$ | H | $C_2H_5$ | H |
| $C_2H_5$ | H | H | $C_2H_5$ |
| $C_2H_5$ | H | $nC_4H_9$ | H |
| $C_2H_5$ | H | H | $nC_4H_9$ |
| $C_2H_5$ | H | $CH_3$ | $CH_3$ |
| $C_2H_5$ | H | $nC_6H_{13}$ | H |
| $C_2H_5$ | H | H | $nC_6H_{13}$ |
| $nC_3H_7$ | H | H | H |
| $tC_4H_9$ | H | H | H |
| $nC_5H_{11}$ | H | H | H |
| $(CH_3)_2CHCH_2CH_2$ | H | H | H |
| $C_2H_5$ | $CH_3$ | H | H |
| $C_2H_5$ | $CH_3$ | $CH_3$ | H |
| $C_2H_5$ | $CH_3$ | H | $CH_3$ |
| —$(CH_2)_3$— | | H | H |
| —$(CH_2)_3$— | | $CH_3$ | H |
| —$(CH_2)_4$— | | $CH_3$ | $CH_3$ |
| —$(CH_2)_4$— | | —$(CH_2)_4$— | |
| —$(CH_2)_4$— | | $nC_4H_9$ | H |
| —$(CH_2)_4$— | | $C_2H_5$ | H |
| —$(CH_2)_4$— | | $nC_6H_{13}$ | H |
| $CH_3$ | H | —$(CH_2)_4$— | |
| $C_2H_5$ | H | —$(CH_2)_4$— | |
| $CH_3$ | $CH_3$ | —$(CH_2)_4$— | |
| $C_6H_5$ | H | —$(CH_2)_4$— | |
| $pCH_3OC_6H_4$ | H | —$(CH_2)_4$— | |
| $pFC_6H_4$ | H | —$(CH_2)_4$— | |
| $pNO_2C_6H_4$ | H | —$(CH_2)_4$— | |
| 2naphthyl | H | —$(CH_2)_4$— | |
| $C_6H_5$ | H | H | H |
| $C_6H_5$ | H | $CH_3$ | H |
| $C_6H_5$ | H | H | $CH_3$ |
| $C_6H_5$ | H | $C_2H_5$ | H |
| $C_6H_5$ | H | H | $C_2H_5$ |
| $C_6H_5$ | H | $CH_3$ | $CH_3$ |
| $pCH_3C_6H_4$ | H | H | H |
| $pCH_3C_6H_4$ | H | $CH_3$ | H |

TABLE I-continued

Antimicrobial Compounds

| R₁ | R₂ | R₃ | R₄ |
|---|---|---|---|
| pCH₃C₆H₄ | H | H | CH₃ |
| pCH₃C₆H₄ | H | C₂H₅ | H |
| pCH₃C₆H₄ | H | H | C₂H₅ |
| pC₂H₅C₆H₄ | H | H | H |
| pC₂H₅C₆H₄ | H | CH₃ | H |
| pC₂H₅C₆H₄ | H | H | CH₃ |
| 2,4xylyl | H | H | H |
| 2,5xylyl | H | H | H |
| pCH₃OC₆H₄ | H | H | H |
| pCH₃OC₆H₄ | H | CH₃ | H |
| pCH₃OC₆H₄ | H | H | CH₃ |
| pCH₃OC₆H₄ | H | C₂H₅ | H |
| pCH₃OC₆H₄ | H | H | C₂H₅ |
| pBrC₆H₄ | H | H | H |
| pClC₆H₄ | H | H | H |
| pClC₆H₄ | H | CH₃ | H |
| pClC₆H₄ | H | H | CH₃ |
| pClC₆H₄ | H | C₂H₅ | H |
| pClC₆H₄ | H | H | C₂H₅ |
| pClC₆H₄ | H | CH₃ | CH₃ |
| pFC₆H₄ | H | H | H |
| pFC₆H₄ | H | CH₃ | H |
| pFC₆H₄ | H | H | CH₃ |
| pFC₆H₄ | H | C₂H₅ | H |
| pFC₆H₄ | H | H | C₂H₅ |
| pNO₂C₆H₄ | H | H | H |
| pNO₂C₆H₄ | H | CH₃ | H |
| pNO₂C₆H₄ | H | H | CH₃ |
| pC₆H₅C₆H₄ | H | H | H |
| 2naphthyl | H | CH₃ | H |
| 2naphthyl | H | H | CH₃ |
| 2naphthyl | H | C₂H₅ | H |
| 2naphthyl | H | H | C₂H₅ |
| C₆H₅ | nC₄H₉ | H | H |
| C₆H₅ | nC₄H₉ | CH₃ | H |
| C₆H₅ | nC₄H₉ | H | CH₃ |
| C₆H₅ | C₆H₅ | C₂H₅ | H |
| CH₃ | H | CH₃OCH₂ | H |
| CH₃ | H | CH₃OCH₂ | H |
| CH₃ | H | H | CH₃OCH₂ |
| CH₃ | H | (CH₃)₂CHOCH₂ | H |
| CH₃ | H | H | (CH₃)₂CHOCH₂ |
| CH₃ | H | nC₄H₉OCH₂ | H |
| CH₃ | H | H | nC₄H₉OCH₂ |
| CH₃ | CH₃ | C₂H₅OCH₂ | H |
| CH₃ | CH₃ | (CH₃)₂CHOCH₂ | H |
| CH₃ | CH₃ | nC₄H₉OCH₂ | H |
| CH₃ | CH₃ | C₆H₅OCH₂ | H |
| C₂H₅ | H | nC₄H₉OCH₂ | H |
| C₂H₅ | H | H | nC₄H₉OCH₂ |
| C₆H₅ | H | CH₃OCH₂ | H |
| C₆H₅ | H | H | CH₃OCH₂ |
| C₆H₅ | H | nC₄H₉OCH₂ | H |
| C₆H₅ | H | H | nC₄H₉OCH₂ |
| —(CH₂)₄— | | (CH₃)₂CHOCH₂ | H |
| —(CH₂)₄— | | nC₄H₉OCH₂ | H |
| CH₃ | CH₃ | (C₂H₅)₂NCH₂ | H |
| 2-naphthyl | H | H | H |

A particularly valuable form of the invention is concerned with the control of microorganisms using chemicals of the formula stated wherein the R's have sets of values shown in TABLE II.

TABLE II

Preferred Antimicrobials

| R₁ | R₂ | R₃ | R₄ |
|---|---|---|---|
| CH₃ | H | C₆H₅ | H |
| CH₃ | H | H | C₆H₅ |
| CH₃ | H | CH₃ | CH₃ |
| C₂H₅ | H | CH₃ | CH₃ |
| C₂H₅ | CH₃ | H | H |
| —(CH₂)₄— | | nC₄H₉ | H |
| CH₃ | H | | —(CH₂)₄— |
| pFC₆H₄ | H | | —(CH₂)₄— |
| C₆H₅ | H | H | H |
| C₆H₅ | H | CH₃ | H |
| C₆H₅ | H | H | CH₃ |
| pCH₃C₆H₄ | H | CH₃ | H |
| pCH₃C₆H₄ | H | H | CH₃ |
| pC₂H₅C₆H₄ | H | H | H |
| pC₂H₅C₆H₄ | H | H | CH₃ |
| pC₂H₅C₆H₄ | H | CH₃ | H |
| pCH₃OC₆H₄ | H | CH₃ | H |
| pCH₃OC₆H₄ | H | H | CH₃ |

TABLE II-continued

Preferred Antimicrobials

| $R_1$ | $R_2$ | $R_3$ | $R_4$ |
|---|---|---|---|
| $pClC_6H_4$ | H | $C_2H_5$ | H |
| $pClC_6H_4$ | H | H | $C_2H_5$ |
| $pFC_6H_4$ | H | $CH_3$ | H |
| $pFC_6H_4$ | H | H | $CH_3$ |
| $pFC_6H_4$ | H | $C_2H_5$ | H |
| $pFC_6H_4$ | H | H | $C_2H_5$ |
| $CH_3$ | H | $CH_3OCH_2$ | H |
| $CH_3$ | H | H | $CH_3OCH_2$ |
| $CH_3$ | H | $nC_4H_9OCH_2$ | H |
| $CH_3$ | H | H | $nC_4H_9OCH_2$ |
| $C_6H_5$ | H | $CH_3OCH_2$ | H |
| $C_6H_5$ | H | H | $CH_3OCH_2$ |
| $-(CH_2)_4-$ | | $nC_4H_9OCH_2$ | H |

In one aspect, the invention is concerned with certain preferred 2,3-dihydro-1,4-dithiin 1,1,4,4-tetroxides believed to be new chemicals, particularly those in which the R's have sets of values as shown in TABLE III.

TABLE III 2,3-Dihydro-1,4-Dithiin 1,1,4,4-Tetroxides

| $R_1$ | $R_2$ | $R_3$ | $R_4$ |
|---|---|---|---|
| $CH_3$ | H | $C_6H_5$ | H |
| $CH_3$ | H | H | $C_6H_5$ |
| $-(CH_2)_4-$ | | $nC_4H_9$ | H |
| $CH_3$ | H | $-(CH_2)_4-$ | |
| $pFC_6H_4$ | H | $-(CH_2)_4-$ | |
| $C_6H_5$ | H | $CH_3$ | H |
| $C_6H_5$ | H | H | $CH_3$ |
| $pCH_3C_6H_4$ | H | $CH_3$ | H |
| $pCH_3C_6H_4$ | H | H | $CH_3$ |
| $pC_2H_5C_6H_4$ | H | $CH_3$ | H |
| $pC_2H_5C_6H_4$ | H | H | $CH_3$ |
| $pCH_3OC_6H_4$ | H | $CH_3$ | H |
| $pCH_3OC_6H_4$ | H | H | $CH_3$ |
| $p-ClC_6H_4$ | H | $C_2H_5$ | H |
| $p-ClC_6H_4$ | H | H | $C_2H_5$ |
| $pFC_6H_4$ | H | $CH_3$ | H |
| $pFC_6H_4$ | H | H | $CH_3$ |
| $pFC_6H_4$ | H | $C_2H_5$ | H |
| $pFC_6H_4$ | H | H | $C_2H_5$ |
| $CH_3$ | H | $CH_3OCH_2$ | H |
| $CH_3$ | H | H | $CH_3OCH_2$ |
| $CH_3$ | H | $nC_4H_9OCH_2$ | H |
| $CH_3$ | H | H | $nC_4H_9OCH_2$ |
| $C_6H_5$ | H | $CH_3OCH_2$ | H |
| $C_6H_5$ | H | H | $CH_3OCH_2$ |
| $-(CH_2)_4-$ | | $nC_4H_9OCH_2$ | H |

A most preferred practice of the invention is directed to the control of fungi, bacteria or viruses on plant life, using 2,3-dihydro-1,4-dithiin 1,1,4,4-tetroxides of the stated formula wherein the R's have the sets of values shown in TABLE IV.

TABLE IV

Preferred Antimicrobial Compounds

| $R_1$ | $R_2$ | $R_3$ | $R_4$ |
|---|---|---|---|
| $C_6H_5$ | H | H | H |
| $C_2H_5$ | $CH_3$ | H | H |
| $CH_3$ | H | $CH_3$ | $CH_3$ |
| $pC_2H_5C_6H_4$ | H | H | H |
| $CH_3$ | H | $C_6H_5$ | H |
| $CH_3$ | H | H | $C_6H_5$ |
| $C_6H_5$ | H | $CH_3OCH_2$ | H |
| $C_6H_5$ | H | H | $CH_3OCH_2$ |
| $pClC_6H_4$ | H | $CH_2CH_3$ | H |
| $pClC_6H_4$ | H | H | $CH_2CH_3$ |
| $pFC_6H_4$ | H | $-(CH_2)_4-$ | |

The last eight listed chemicals of TABLE IV constituted a preferred class of new chemicals.

The 2,3-dihydro-1,4-dithiin 1,1,4,4-tetroxides with which the invention is concerned may be made, for example, either by oxidation of the corresponding dithiin, or by oxidative decarboxylation of dithiin carboxylic acids.

Particularly preferred antimicrobial compounds employed in the invention are 2,3-dihydro-5-phenyl-1,4-dithiin 1,1,4,4-tetroxide, 2-ethyl-5,6-dihydro-3-methyl-1,4-dithiin 1,1,4,4-tetroxide, 2,3-dihydro-2,3,5-trimethyl-1,4-dithiin 1,1,4,4-tetroxide, 2-(4-ethylphenyl)-5,6-dihydro-1,4-dithiin 1,1,4,4-tetroxide, 2,3-dihydro-5-methyl-2-phenyl-1,4-dithiin 1,1,4,4-tetroxide, 2,3-dihydro-5-methyl-2-phenyl-1,4-dithiin 1,1,4,4-tetroxide, 2,3-dihydro-2-methoxymethyl-5-phenyl-1,4-dithiin 1,1,4,4-tetroxide, 2,3-dihydro-2-methoxymethyl-6-phenyl-1,4-dithiin 1,1,4,4-tetroxide, 2-(4-chlorophenyl)-5-ethyl-5,6-dihydro-1,4-dithiin 1,1,4,4-tetroxide and 2-(4-chlorophenyl)-6-ethyl-5,6-dihydro-1,4-dithiin 1,1,4,4-tetroxide. The last seven compounds are particularly valuable new chemicals.

For use in controlling fungi, particularly effective compounds are 2,3-dihydro-5-phenyl-1,4-dithiin 1,1,4,4-tetroxide, 2-(4-ethylphenyl)-5,6-dihydro-1,4-dithiin 1,1,4,4-tetroxide, 2,3-dihydro-5-methyl-3-phenyl-1,4-dithiin 1,1,4,4-tetroxide, 2,3-dihydro-5-methyl-2-phenyl-1,4-dithiin 1,1,4,4-tetroxide, 2,3-dihydro-2,3,5-trimethyl-1,4-dithiin 1,1,4,4-tetroxide, 2,3-dihydro-2-methoxymethyl-5-phenyl-1,4-dithiin 1,1,4,4-tetroxide, 2,3-dihydro-2-methoxymethyl-6-phenyl-1,4-dithiin 1,1,4,4-tetroxide, 2-(4-chlorophenyl)-5-ethyl-5,6-dihydro-1,4-dithiin 1,1,4,4-tetroxide and 2-(4-chlorophenyl)-6-ethyl-5,6-dihydro-1,4-dithiin 1,1,4,4-tetroxide.

Preferred chemicals for use in the control of bacteria are 2,3-dihydro-5-phenyl-1,4-dithiin 1,1,4,4-tetroxide, 2,3-dihydro-2,3,5-trimethyl-1,4-dithiin 1,1,4,4-tetroxide, and the new chemicals 2,3-dihydro-5-methyl-3-phenyl-1,4-dithiin 1,1,4,4-tetroxide and 2,3-dihydro-5-methyl-2-phenyl-1,4-dithiin 1,1,4,4-tetroxide.

As agents for the control of viruses, preferred compounds are 2-ethyl-5,6-dihydro-3-methyl-1,4-dithiin 1,1,4,4-tetroxide and 2-(4-fluorophenyl)-4a,5,6,7,8,8a-hexahydro-1,4-benzodithiin; the latter is a new chemical.

Dithiins and dithiin acids may be prepared, for example, by two broad methods:

I. Reaction of an alpha-halocarbonyl compound such as an alpha-haloketone or an alpha-haloester with a 1,2-dithiol, either in a basic followed by an acid medium (Method Ia), or in an acid medium throughout (Method Ib).

II. Reaction of a 1,2-dithiol with a ketone or aldehyde having an alpha-methylene group or with a beta-ketoester, followed by halogenation and ring expansion of the dithiolane so produced (Method II).

In certain cases the method of preparation employed may lead to a mixture of two different isomers of a particular chemical. Such an isomeric mixture may be used directly if desired for fungicidal, bactericidal, or viricidal purpose in accordance with the invention. Resolution of the mixture into products richer in one or the other of the isomers may be undertaken, but is not necessary. Also, if desired, individual isomers may be prepared separately by a suitable synthetic method and employed as fungicides, bactericides or viricides as described below.

The herein described 2,3-dihydro-1,4-dithiin 1,1,4,4-tetroxides are surprisingly effective agents for combatting organisms that cause plant disease. In particular, these chemicals are highly active against fungi such as Pythium sp. and *Rhizoctonia solani* (Kuhn), which cause seed rot and seedling decay in the majority of seeded crops. Application of the chemicals as seed protectants is the preferred method but in certain cases applications on or within the soil surrounding the plants may be advantageous.

These compounds are also highly active against the tomato pathogen, *Alternaria solani* (Ell. and G. Marten) Sor., which causes a damaging foliage blight. Foliar application of these chemicals is safe to plants at dosages which are effective for disease control.

Chemicals of the invention are also effective antibacterials. Antibacterials are important in the treatment of plant, animal or human diseases. The compounds are also useful for certain industrial applications, such as paint and coating preservatives, fabric treatments to prevent microbial damage, or as water treatments for slime control.

Chemicals of the invention also find utility as plant virus disease inhibitors when used as chemotherapeutic treatments.

The chemicals employed in this invention possess a high degree of bactericidal activity controlling such bacteria as *Pseudomonas aeruginosa* (Schroeter) Migula, *Escherichia coli* (Migula) Castellani and Chalmers, *Staphylococcus aureus* Rosenbach, *Xanthomonas phaseoli* (Smith) Dowson and *Erwinia amylovora* (Burrill) Winslow et al.

The chemicals employed in this invention also control fungi such as *Alternaria solani* (Ellis and Mastin).

The activity of the present virus control agents is noted particularly in connection with mosaic type viruses which include Southern Bean Mosaic virus, Common Bean Mosaic virus, Pea Mosaic virus, Tobacco Mosaic virus, Cucurbit Mosaic virus, Maize Mosaic virus, Lettuce Mosaic virus, Wheat Mosaic Virus, Sugar Beet Mosaic virus, Alfalfa Mosaic virus, Beet Mosaic virus, Peach Mosaic virus, etc. Viruses of the Ringspot types such as Tobacco Ringspot virus and Tomato Ringspot virus may also be mentioned.

In agricultural applications, the chemical may be applied directly to plants (e.g., seeds, foliage) or to soil in which plant life is growing or is to be grown, to protect the plant life against the harmful effects of such pathogenic microorganisms as bacteria, fungi, and viruses. For example, the chemical may be applied as a coating to seeds by tumbling the chemical with the seeds, either alone or in admixture with a powdered solid carrier. Typical powdered solid carriers are the various mineral silicates, e.g., mica, talc, pyrophyllite, and clays. The chemical may also be applied to the seeds in admixture with a conventional surface-active wetting agent, with or without additional powdered solid carrier, as by first wetting the mixture with a small amount of water and then tumbling the seeds in the slurry. The surface-active wetting agents that may be used with the chemical may be any of the conventional anionic, non-ionic, or cationic surface-active agents. Such surfact-active agents are well known and reference is made to U.S. Pat. No. 2,547,724, columns 3 and 4, for detailed examples of the same. As a seed protectant, the amount of the chemical coated on the seeds will be ¼ to 12 ounces per hundred pounds of the seed. As a soil treatment for fungi and the like, the chemical may be applied (a) as a dust in admixture with sand or soil or a powdered solid carrier such as a mineral silicate, with or without an additional surface-active wetting agent, to the furrows with the planting of the seeds, or (b) the chemical may be applied as an aqueous spray, if desired including a surface-active dispersing agent and a powdered solid carrier, to the seed rows before, or with, or after planting the seeds. As a soil treatment, the amount of the chemical applied to the seed rows will be from 0.1 to 10 pounds per acre based on rows 2 inches wide and 2 inches deep a distance of 40 inches apart. Also, as a soil treatment, the chemical may be applied broadcast as a similar dust or aqueous spray with an application rate of 1 to 100 pounds per acre. As a foliage treatment (e.g., fungicidal or bactericidal, the chemical may be applied to growing plants at a rate of ¼ to 10 pounds per acre. Such application is generally as an aqueous spray which also contains a surface-active dispersing agent, with or without a powdered solid carrier or hydrocarbon solvent. These sprays usually are repeated at time intervals ranging from three days to two weeks during the growing season. Typical formulations are as follows:

a. emulsifiable concentrate:
   48.1% 2,3-Dihydro-1,4-dithiin 1,1,4,4-tetroxide
   11.1% Surfactant (e.g., Tween (trademark) 80; polyoxyethylene sorbitan monooleate)
   40.8% Xylene
   100.0% Total b. Wettable powder:
   75.0% 2,3-Dihydro-1,4-dithiin 1,1,4,4-tetroxide
   2.0% Triton (trademark) X-120
   2.0% Daxad (trademark) - 11
   21.0% Dixie clay
   100.0% Total Triton X-120 is an alkylaryl polyether alcohol (9-10 moles polyethylene oxide) in dry powered form (40% active on an insoluble carrier). The active ingredient in Triton X-120 is Triton X-100, which is a liquid nonionic surfactant (isooctylphenylpolyethoxyethanol, obtained by condensing the alkylphenylphenol with ethylene oxide). Daxad-11 is polymerized sodium salt of alkylnaphthalene sulfonic acid (more particularly, the sodium salts of dinaphthylmethane sulfonic acids obtained from naphthalene, sulfuric acid and formaldehyde, according to U.S. Pat. No. 1,336,759, Schmidt, Apr. 13, 1920).

As industrial bactericides and fungicides, the present chemicals may be used to control bacteria or fungi by contacting the bacteria or fungi with the chemical in any suitable manner. Materials capable of nourishing bacteria and fungi may be protected from destruction by such pests by contacting, mixing, or impregnating with the chemical. Such materials include petroleum oils, fuel oils, fabrics, cellulosic materials in various forms including textiles, wood, paper, etc. In order to broaden their spectrum or increase their effect the chemicals may be combined with other pesticidal control agents such as fungicides, bactericides, insecticides or miticides.

Chemicals of this invention may be used as antimicrobial agents for the preservation of petroleum hydrocarbons. Petroleum hydrocarbons are known to be utilized by bacteria and fungi as a food source. The resulting increase in microbial population can cause various problems such as filter plugging, metal corrosion of storage tanks and aircraft fuel tanks, fuel line plugging and flame-outs. A biocide added to hydrocarbon fuel can prevent microbial growth and eliminate the problems mentioned.

Chemicals of this invention may be used as material preservatives against cellulose-degrading fungi causing deterioration of textiles, paper, wood, etc.

The chemicals of the invention may be incorporated in soap to be used in combatting bacteria and fungi.

The chemicals containing alklyaminomethyl groups are frequently conveniently formulated in the form of their equivalent salts (e.g., hydrochlorides, acetates, citrates), which are readily provided by treatment with an appropriate acid.

The following examples, in which all quantities are expressed by weight unless otherwise indicated, will serve to illustrate the practice of the invention in more detail.

EXAMPLE 1

(Method Ia)

Ethanedithiol (94 g, 1 mole) was dissolved in benzene (500 ml) and triethylamine (101 g, 1 mole) added. To the stirred, cooled solution was added phenacyl bromide (199 g, 1 mole) in benzene (500 ml) dropwise over several hours. The reaction mixture became semi-solid. Water (200 ml) was added with agitation, the organic layer separated and washed with dilute HCl (3 × 200 ml.) dried over $MgSO_4$ and refluxed under a Dean-Stark trap with a trace of p-toluenesulfonic acid. When no more water collected, the solution was cooled, washed with ice-cold dilute caustic soda (100 ml) and water (100 ml) and reduced in volume under vacuum to a yellowish oil. This solidified on refrigeration; it was recrystallized from a small quantity of ethanol to give 2,3-dihydro-5-phenyl-1,4-dithiin as white needles, m.p. 54°-55°, 124 g (64%).

(Method Ib)

Ethanedithiol (94 g, 1 mole) was dissolved in benzene (500 ml) containing a trace of p-toluenesulfonic acid and the solution was refluxed under a Dean-Stark trap. Phenacyl chloride (154.5 g, 1 mole) dissolved in the minimum quantity of benzene was added dropwise to the refluxing solution over a period of two hours. Water began to collect immediately. After addition was complete, refluxing was continued for a further three hours, after which time substantially one mole water had collected in the trap. The solution was cooled, washed with ice-cold dilute caustic soda (3 × 300 ml), water (2 × 300 ml) and dried over magnesium sulfate. The clear solution was concentrated in vacuo to a colorless gum, which solidified on standing to a white mass of crystals, m.p. 48°-52°, yield 132 g (68%).

(Method II)

Ethanedithiol (94 g) and acetophenone (120 g, 1 mole) were dissolved in benzene (500 ml), a trace of pTSA added and the solution refluxed under a Dean-Stark trap for 16 hours, until no more water collected. The solution was cooled, washed with ice-cold dilute caustic soda, then water, and reduced in volume to a viscous, colorless, or yellowish oil. This was distilled under vacuum to give 2-methyl-2-phenyl-1,3-dithiolane as a colorless oil with an unpleasant odor, yield 120 g (61%).

The dithiolane (19.6 g, 0.1 mole) was dissolved in benzene (100 ml) and bromine (16 g, 0.1 mole) dissolved in a little benzene, was added to the stirred, cooled solution, followed by triethylamine (20.2 g, 0.2 mole). The solution, which quickly precipitated a mass of needle-like crystals, was washed with water (200 ml), dilute HCl (2 × 200 ml) and water (200 ml) and then reduced in volume to a smelly, viscous oil. This partially solidified on freezing. It was washed with a small quantity of ice-cold absolute ethanol, then recrystallized from a small quantity of ethanol to give 2,3-dihydro-5-phenyl-1,4-dithiin as white needles, m.p. 53°-54°, yield 10.8 g (56%), melting-point undepressed by mixture with material from Method I.

2,3-Dihydro-5-phenyl-1,4-dithiin (19.4 g. 0.1 mole) was dissolved in the minimum quantity of glacial acetic acid, and added dropwise to a refluxing mixture of 35% hydrogen peroxide (60 cc) and glacial acetic acid (60 ml). There was vigorous reaction as each drop was added. When addition was complete, a solid began to appear; the suspension was warmed on a hot-plate for a further 15 minutes, then refrigerated. The white crystalline solid which appeared was collected, washed with water and recrystallized from glacial acetic acid to give 2,3-dihydro-5-phenyl-1,4-dithiin 1,1,4,4-tetroxide as short white needles, m.p. 205.5°–206.5°, yield 18.3 g (71%).

2,3-Dihydro-5-phenyl-1,4-dithiin (19.4 g), dissolved in the minimum quantity of glacial acetic acid, was added dropwise to a 40% solution of peracetic acid in acetic acid (90 cc) in an ice-bath. There was a vigorous, exothermic reaction as each drop was added. As addition proceeded, a white solid appeared; when addition was complete the mixture was left in the ice-bath for a further 2 hours, then overnight at room temperature. The solid was collected, washed with water and recrystallized to give a 90% yield of a material identical to that prepared with dydrogen peroxide.

EXAMPLE 2

(Method I$b$)

Ethanedithiol (94 g) and ethyl alpha-chloroacetoacetate (164.5 g) were dissolved in benzene (500 g), a trace of p-toluenesulfonic acid added, and the whole solution refluxed under a Dean-Stark trap for one hour, when 16 cc of water had collected. The solution was cooled, washed with ice-cold dilute caustic soda and the benzene removed in vacuo. Ethanolic caustic soda (80 g in the minimum amount of ethanol) was added and the solution refluxed for 30 minutes, then cooled, diluted with water (one volume), and made acid with dilute HCl. The thick white precipitate was filtered, washed with water and recrystallized from ethanol to give 5,6-dihydro-3-methyl-1,4-dithiin-2-carboxylic acid as long white needles, m.p. 173°–175°, yield 92 g (52%).

5,6-Dihydro-3-methyl-1,4-dithiin-2-carboxylic acid (17.6 g) was dissolved in the minimum quantity of warm acetic acid, and added to a refluxing mixture of 35% hydrogen peroxide (50 cc) and acetic acid (50 cc). There was a vigorous reaction. On cooling a white solid appeared, which was filtered, washed with water and recrystallized from absolute ethanol to give 2,3-dihydro-5-methyl-1,4-dithiin 1,1,4,4-tetroxide as white needles, m.p. 231°–235°, yield 10.4 (53%)

EXAMPLE 3

(Method I$b$)

To a solution of chloroacetaldehyde dimethyl acetal (49.6 g) in benzene (300 ml) was added a trace of p-toluenseulfonic acid, water (7.2 g) and ethanedithiol (37.6 g). The mixture was stirred for two hours at room temperatures, left overnight and then refluxed under a Dean-Stark trap. The reaction mixture was then cooled, washed with dilute caustic soda and water, and dried. The benzene was removed under vacumm and the resultant oily liquid distilled under reduced pressure to give 2,3-dihydro-1,4-dithiin as a colorless, smelly liquid b.p. 88°–90°/5mm, yield 14 g (30%).

To a stirred relfuxing solution of 30% hydrogen peroxide (91 ml) and glacial acetic acid (90 cc) was added dropwise 2,3-dihydro-1,4-dithiin (12 g) in a little glacial acetic acid. There was a vigorous reaction. The solution was refluxed for a further half hour, then refrigerated. The white solid 2,3-dihydro-1,4-dithiin 1,1,4,4-tetroxide which appeared was filtered, washed with water and then ethanol. Yield 15.6 g (84%), m.p. > 280°(d).

EXAMPLE 4

(Method I$b$)

Ethanedithiol (94 g, 1 mole) was mixed with 1-chloro-2-butanone (106.5 g, 1 mole) and a trace of p-toluenesulfonic acid at ice-bath temperature. The mixture was stirred in the ice-bath for six hours, then allowed to warm to room temperature. Benzene (200 cc) was added, water (18 cc) separated and discarded, and the solution refluxed briefly under a Dean-Stark trap. A further 1.5 cc water collected. The solution was cooled, washed with ice-cold dilute caustic soda and water, dried and reduced in volume to a gum which was distilled at reduced pressure to give 2-ethyl-5,6-dihydro-1,4-dithiin as a colorless, smelly oil, b.p. 63°–64°/1 mm, yield 92 g (62%).

2-Ethyl-5,6-dihydro-1,4-dithiin was oxidized by hydrogen peroxide and glacial acetic acid as described above, to give 2-ethyl-5,6-dihydro-1,4-dithiin, 1,1,4,4-tetroxide as white needles, m.p. 188.5°–189.5°.

EXAMPLE 5

2-(4-Ethylphenyl)-5,6-dighydro-1,4-dithiin was made by Method I$b$ using ethane dithiol and 4-ethylphenacyl bromide. It was oxidized by glacial acetic acid and hydrogen peroxide as described above to give 2-(4-ethylphenyl)-5,6-dihydro-1,4-dithiin 1,1,4,4-tetroxide as white plates, m.p. 186.5°–190°.

EXAMPLE 6

2,3-Dihydro-5methyl-2(or 3)-phenyl-1,4-dithiin was made by Method I$b$ using 1,2-dimercapto-1-phenyethane and chloroactone. It was oxidized by peractic acid as described above to give 2,3-dihydro-5-methyl-2(or 3)-phenyl-1,4-dithiin 1,1,4,4-tetroxide as white crystals, m.p. 160°–170°.

EXAMPLE 7

2,3-Dihydro-2-methoxymethyl-5(or 6)-phenyl-1,4-dithiin was made by Method I$b$ using 1,2-dimercapto-3-methoxypropane and phenacyl bromide. It was oxidized by peracetic acid as described above to give white crystals of 2,3-dihydro-2-methoxymethyl-5(or 6)-phenyl-1,4-dithiin 1,1,4,4-tetroxide, m.p. 116°–118°.

EXAMPLE 8

2-(4-Chlorophenyl)-5(or 6)-ethyl-5,6-dihydro-1,4dithiin was made by Method I$a$ using butane-1,2-dithiol and 4-chlorophenacyl bromide. It was oxidized by peractic acid as described above to give 2-(4-chlorophenyl)-5(or 6)-ethyl-5,6-dihydro-1,4-dithiin 1,1,4,4-tetroxide as white crystals, m.p. 120°–130°.

EXAMPLES 9–83

The procedures of the foregoing Examples are repeated, with subtstitution of appropriate starting materials, to produce the additional products listed as Examples 9–83 in TABLE V, which identifies the substituents in the general formula stated above and gives melting point and analytical data for all products, including those of Examples 1–8. In TABLE V an asterisk (*) between the $R_3$ and $R_4$ substituents indicates that the product is a mixture of two isomers wherein the $R_3$ and $R_4$ substituents are interchanged. Additional analytical data on certain of the products are as follows:

Example 42: N, Calc. 3.92; Found 4.35
Example 63; N, Calc. 4.61; Found 4.65, 4.60
Example 64; N, Calc. 4.42; Found 4.50

Example 79 (as the hydrochloride salt):

N, Calc. 4.22; Found 4.19
Cl, Calc. 10.41; Found 11.05, 9.50.

In subsequent Examples, the chemicals are identified by the example numbers assigned in TABLE V.

In certain of the preparations listed in TABLE V, a starting chemical was used which was believed to have a specific isomeric configuration, and, accordingly, in those cases the product is presumed to be an isomer having the corresponding specific structure. Thus, the Example 14, 15, 22 46 chemicals were prepared from what was believed to be meso-2,3-butanedithiol (and are accordingly believed to have the cis structure), while the Example 16, 20, 32 and 59 chemicals were prepared from what was believed to be threo-1,2-butanedithiol (and are accordingly believed to have the trans structure). The products in which $R_3$ and $R_4$ together form $-CH_2)_4-$ were made from what was believed to be trans-1,2-cyclohexanedithiol. However, for purposes of the invention it is not necessary to employ a specific isomer, since satisfactory results are obtained with either isomer or with mixed products, as points out previously.

TABLE V

Examples 1–83

| Ex. | $R_1$ | $R_2$ | $R_3$ | $R_4$ | MP (° C.) | Calc. C | Calc. H | Found C | Found H |
|---|---|---|---|---|---|---|---|---|---|
| 3 | H | H | H | H | >290 | 26.38 | 3.32 | 26.66 / 26.48 | 3.33 / 3.30 |
| 2 | $CH_3$ | H | H | H | 231–235 | 30.61 | 4.08 | 30.83 / 30.58 | 4.23 / 4.16 |
| 9 | $CH_3$ | H | $CH_3$ | * H | 160–205 | 34.29 | 4.76 | 34.85 / 33.23 | 4.81 / 4.58 |
| 10 | $CH_3$ | $CH_3$ | $nC_6H_{13}$ | H | 73–75 | 48.97 | 7.54 | 48.83 / 48.67 | 7.59 / 7.63 |
| 11 | $CH_3$ | H | $C_2H_5$ | * H | 111–142 | 37.50 | 5.40 | 37.41 / 37.60 | 5.63 / 5.20 |
| 12 | $CH_3$ | $CH_3$ | $nC_8H_{17}$ | H | 75–78 | 52.16 | 8.13 | 52.09 / 51.96 | 7.89 / 7.82 |
| 6 | $CH_3$ | H | $C_6H_5$ | * H | 160–170 | 48.53 | 4.40 | 48.35 / 47.70 | 4.59 / 4.33 |
| 13 | $CH_3$ | H | $C_8H_{17}$ | * H | 83–113 | | | | |
| 14 | $CH_3$ | H | $CH_3$ | $CH_3$ | 151–164 | 37.50 | 5.40 | 37.41 / 37.39 | 5.27 / 5.32 |
| 15 | $CH_3$ | $CH_3$ | $CH_3$ | $CH_3$ | 141.5–143 | 40.34 | 5.92 | 40.46 | 5.98 |
| 4 | $C_2H_5$ | H | H | H | 188.5–189.5 | 34.29 | 4.76 | 34.06 / 34.55 | 4.79 / 4.90 |
| 16 | $CH_3$ | $CH_3$ | $CH_3$ | $CH_3$ | 243–245.5 | 40.34 | 5.92 | 40.39 | 6.15 |
| 17 | $C_2H_5$ | H | $CH_3$ | * H | 141–153 | 37.50 | 5.40 | 37.79 / 37.59 | 5.29 / 5.23 |
| 18 | $C_2H_5$ | H | $C_2H_5$ | * H | 99–136 | 40.34 | 5.92 | 39.90 / 40.31 | 5.84 / 5.90 |
| 19 | $C_2H_5$ | H | $C_4H_9$ | * H | 128–130 | 45.11 | 6.81 | 45.31 / 45.36 | 7.35 / 7.38 |
| 20 | $C_2H_5$ | H | $CH_3$ | $CH_3$ | 128–132 | 40.34 | 5.92 | 40.64 | 5.72 |
| 21 | $C_2H_5$ | H | $C_6H_{13}$ | * H | 138–141.5 | 48.97 | 7.54 | 48.75 / 48.67 | 7.87 / 7.69 |
| 22 | $C_2H_5$ | H | $CH_3$ | $CH_3$ | 89–91 | 40.34 | 5.92 | 40.07 | 5.78 |
| 23 | $nC_3H_7$ | H | H | H | 181–182.5 | 37.50 | 5.40 | 37.80 / 37.65 | 5.66 / 5.66 |
| 24 | tBu | H | H | H | 209–213 | 40.34 | 5.92 | 40.68 | 5.99 |
| 25 | $nC_5H_{11}$ | H | H | H | 205–206.5 | 42.86 | 6.35 | 42.12 / 42.16 | 6.15 / 6.11 |
| 26 | $(CH_3)_2CH(CH_2)_2$ | H | H | H | 233–235 | 42.86 | 6.35 | 43.01 / 43.29 | 6.51 / 6.68 |
| 27 | $C_2H_5$ | $CH_3$ | H | H | 109–113 | 37.50 | 5.40 | 37.82 / 38.17 | 5.28 / 5.44 |
| 28 | $C_2H_5$ | $CH_3$ | $CH_3$ | * H | oil | 40.34 | 5.92 | 40.53 | 5.83 |
| 29 | | $(CH_2)_3$ | H | H | 222–226 | 37.84 | 4.50 | 37.43 / 37.73 | 4.45 / 4.56 |
| 30 | | $(CH_2)_3$ | $CH_3$ | H | 158–161 | 40.68 | 5.08 | 40.00 / 40.65 | 5.16 / 5.00 |
| 31 | | $(CH_2)_4$ | | $(CH_2)_4$ | 260–262 | 49.65 | 6.25 | 49.96 | 6.37 |
| 32 | | $(CH_2)_4$ | $CH_3$ | $CH_3$ | 192–195 | 45.45 | 6.10 | 44.60 | 5.98 |
| 33 | | $(CH_2)_4$ | $C_4H_9$ | H | 91–94.5 | 49.31 | 6.90 | 49.28 / 49.03 | 6.84 / 7.03 |
| 34 | | $(CH_2)_4$ | $C_2H_5$ | H | 163–164 | 45.45 | 6.10 | 45.10 / 45.42 | 5.87 / 5.90 |
| 35 | | $(CH_2)_4$ | $C_6H_{13}$ | H | 73–76 | 52.49 | 7.55 | 52.50 / 52.06 | 7.49 / 7.47 |
| 36 | $CH_3$ | H | | $(CH_2)_4$ | 164–165 | 43.20 | 5.64 | 43.27 | 5.48 |
| 37 | $C_2H_5$ | H | | $(CH_2)_4$ | 140–142 | 45.45 | 6.10 | 45.82 | 6.13 |

TABLE V-continued

Examples 1–83

| Ex. | $R_1$ | $R_2$ | $R_3$ | $R_4$ | MP (°C.) | Calc. C | Calc. H | Found C | Found H |
|---|---|---|---|---|---|---|---|---|---|
| 38 | $CH_3$ | $CH_3$ | | $(CH_2)_4$ | 191–193 | 45.45 | 6.10 | 45.65 | 6.29 |
| 39 | $C_6H_5$ | H | | $(CH_2)_4$ | 202–204 | 53.84 | 5.16 | 54.28 | 5.26 |
| 40 | $pMeOC_6H_9$ | H | | $(CH_2)_4$ | 192–193 | 52.63 | 5.30 | 52.66 | 5.57 |
| 41 | $pFC_6H_4$ | H | | $(CH_2)_4$ | 170.5–172.5 | 50.89 | 4.57 | 50.83 | 4.58 |
| 42 | $pNO_2C_6H_4$ | H | | $(CH_2)_4$ | 214.5–217.5 | 47.06 | 4.23 | 47.37 | 4.30 |
| 43 | 2naphthyl | H | | $(CH_2)_4$ | 190.5–194 | 59.66 | 5.01 | 59.92 | 5.14 |
| 1 | $C_6H_5$ | H | H | H | 205.5–206.5 | 46.06 | 3.93 | 46.57 46.29 | 3.99 3.78 |
| 44 | $C_6H_5$ | H | $CH_3$ | * H | 150–175 | 48.53 | 4.44 | 48.72 48.39 | 4.49 4.42 |
| 45 | $C_6H_5$ | H | $C_2H_5$ | * H | 125–165 | 50.35 | 4.90 | 50.86 51.11 | 5.11 5.13 |
| 46 | $C_6H_5$ | H | $CH_3$ | $CH_3$ | 106–112 | 50.35 | 4.90 | 50.68 50.28 | 5.02 5.16 |
| 47 | $pCH_3C_6H_4$ | H | H | H | 255–260 | 48.53 | 4.44 | 49.19 49.07 | 4.56 4.65 |
| 48 | $pCH_3C_6H_4$ | H | $CH_3$ | * H | 203–205 | 50.35 | 4.90 | 50.48 50.11 | 5.22 5.29 |
| 49 | $pCH_3C_6H_4$ | H | $C_2H_5$ | * H | 119–137 | 52.00 | 5.37 | 52.27 52.18 | 5.44 5.39 |
| 5 | $pC_2H_5C_6H_4$ | H | H | H | 186.5–190 | 50.35 | 4.90 | 50.38 | 4.83 |
| 50 | $pC_2H_5C_6H_4$ | H | $CH_3$ | * H | 155–165 | 52.00 | 5.33 | 51.70 51.76 | 4.86 4.53 |
| 51 | 2,4xylyl | H | H | H | 216–221 | 50.35 | 4.90 | 50.60 50.38 | 5.01 5.11 |
| 52 | 2,5xylyl | H | H | H | 203–205 | 50.35 | 4.90 | 50.63 | 5.12 |
| 53 | $pCH_3OC_6H_4$ | H | H | H | 188–189 | 45.83 | 4.17 | 45.33 45.40 | 4.10 4.15 |
| 54 | $pCH_3OC_6H_4$ | H | Et | * H | 122–130 | 49.37 | 5.10 | 49.49 49.27 | 5.39 5.42 |
| 55 | $pCH_3OC_6H_4$ | H | Me | * H | 153–171 | 47.68 | 4.64 | 47.47 47.87 | 4.46 4.51 |
| 56 | $pBrC_6H_4$ | H | H | H | 223(d) | 35.61 | 2.67 | 36.07 35.63 | 3.09 2.74 |
| 57 | $pClC_6H_4$ | H | H | H | 240–241 | 41.30 | 3.03 | 41.50 41.27 | 3.37 3.24 |
| 58 | $pClC_6H_4$ | H | $CH_3$ | * H | 195–200 | 43.25 | 3.60 | 43.69 43.54 | 3.34 3.39 |
| 8 | $pClC_6H_4$ | H | $C_2H_5$ | * H | 120–130 | 44.93 | 4.06 | 45.05 45.43 | 4.10 4.20 |
| 59 | $pClC_6H_4$ | H | $CH_3$ | $CH_3$ | 182–183 | 44.93 | 4.06 | 45.28 | 4.03 |
| 60 | $pFC_6H_4$ | H | H | * H | 245–247 | 43.48 | 3.26 | 43.73 44.26 | 3.09 3.37 |
| 61 | $pFC_6H_4$ | H | $CH_3$ | * H | 176–182 | 45.52 | 3.79 | 46.27 46.01 | 3.91 3.91 |
| 62 | $pFC_6H_4$ | H | $C_2H_5$ | * H | 122–167 | 47.45 | 4.28 | 47.96 | 4.24 |
| 63 | $pNO_2C_6H_4$ | H | H | H | 255–260(d) | 39.51 | 2.97 | 39.51 39.64 | 2.98 2.97 |
| 64 | $pNO_2C_6H_4$ | H | $CH_3$ | * H | 219–222.5 | 41.64 | 3.47 | 42.31 | 3.38 |
| 65 | $pC_6H_5C_6H_4$ | H | H | H | 261–262 | 57.49 | 4.19 | 58.69 58.05 | 4.67 4.56 |
| 66 | 2naphthyl | H | $CH_3$ | * H | 162–184 | | | | |
| 67 | 2naphthyl | H | $C_2H_5$ | * H | 163–188 | 57.14 | 4.80 | 56.90 56.90 | 4.59 4.57 |
| 68 | $C_6H_5$ | $nC_4H_9$ | H | H | 139–141 | 53.50 | 5.77 | 53.53 | 5.80 |
| 69 | $C_6H_5$ | $nC_4H_9$ | $CH_3$ | * H | 98–102 | 54.87 | 6.14 | 54.72 | 6.09 |
| 70 | $C_6H_5$ | $C_6H_5$ | $C_2H_5$ | H | 145–148 | 59.83 | 4.71 | 59.70 60.06 | 4.95 5.01 |
| 71 | $CH_3$ | H | $CH_3OCH_2$ | * H | 88–112 | 35.01 | 5.04 | 34.95 34.77 | 5.06 5.06 |
| 72 | $CH_3$ | H | $(CH_3)_2CHOCH_2$ | * H | 75–88 | 40.30 | 6.01 | 40.16 39.48 | 5.80 5.70 |
| 7 | $C_6H_5$ | H | $CH_3OCH_2$ | * H | 116–118 | 47.69 | 4.67 | 46.98 47.02 | 4.94 5.04 |
| 73 | $CH_3$ | H | $nC_4H_9OCH_2$ | * H | 83–90 | 42.55 | 6.38 | 43.48 42.64 | 6.40 6.55 |
| 74 | $C_2H_5$ | H | $nC_4H_9OCH_2$ | * H | 65–72 | 44.59 | 6.80 | 43.88 43.83 | 6.87 6.82 |
| 75 | $C_6H_5$ | H | $nC_4H_9OCH_2$ | * H | 109–119 | | | | |
| 76 | $CH_3$ | $CH_3$ | $nC_4H_9OCH_2$ | H | oil | 44.59 | 6.76 | 45.90 | 6.96 |
| 77 | $(CH_2)_4$ | | $nC_4H_9OCH_2$ | H | oil | | | | |
| 78 | $(CH_2)_4$ | | $(CH_3)_2CHOCH_2$ | H | 89– | 46.75 | 6.54 | 44.36 | 5.86 |

TABLE V-continued

Examples 1-83

| Ex. | R₁ | R₂ | R₃ | R₄ | MP (°C.) | Calc. C | Calc. H | Found C | Found H |
|---|---|---|---|---|---|---|---|---|---|
| 79 | CH₃ | CH₃ | (C₂H₅)₂NCH₂ | H | 98 157–162 | 39.82 | 6.64 | 44.64 38.83 38.81 | 5.95 6.51 6.46 |
| 80 | CH₃ | CH₃ | C₂H₅OCH₂ | H | 130–134 | 40.30 | 6.01 | 41.13 40.22 | 5.98 5.79 |
| 81 | CH₃ | CH₃ | (CH₃)₂CHOCH | H | 96–98 | 42.55 | 6.43 | 42.47 42.36 | 6.32 6.25 |
| 82 | CH₃ | CH₃ | PhOCH₂ | H | 155.5–158 | 49.37 | 5.10 | 49.67 49.57 | 5.12 5.14 |
| 83 | 2naphthyl | H | H | H | 254.5–255.5 | 54.55 | 3.92 | 54.98 55.14 | 3.84 3.99 |

EXAMPLE 84

Control of corn seedling diseases caused by fungi such as Rhizoctonia, Rythium and Fusarium by seed treatment with dithiin tetroxides.

Chemicals of the inventions were applied to corn seeds (Var. Leaming Fodder) by tumbling the seeds with the appropriate amounts of chemical and carrier (e.g., 43.7 mg. to 175 mg. of chemical with equal amounts of dixie clay) to give rates of 1 to 4 oz. of active ingredient per 100 pounds of seed.

Seventy gram seed lots were treated by tumbling seeds and chemical in glass jars on a vertical turntable for 20 minutes, at which time the seeds were well coated with the chemical.

Seeds were planted in flats of soil, which were naturally infested with desease producing organisms. Eight replicatons of each planting, 25 seeds per row, were made with one replication of each treatment in a given flat. After planting, each flat of soil was wetted with a measured amount of water (one liter), then placed in a controlled temperature chamber (55° F.) for 10 days to promote desease development.

Flats were then transferred to a normal greenhouse environment (75° F.) where the seeds continued germination and growth for 1 week. At this time th seedlings were counted and the value of the chemical protectant was assessed on the basis of the percentage germination compared to the untreated control. The formula for this determination was as follows:

$$\% G = \frac{ES}{SP} \times 100$$

wherein % G stands for percent germination, ES stands for the number of emerged seedlings and SP stands for the number of seeds planted.

The results are shown in TABLE VI, wherein the test chemicals are identified by example numbers corresponding to those in TABLE V.

TABLE VI

CONTROL OF CORN SEEDLINGS DISEASE BY SEED TREATMENT WITH DITHIIN TETROXIDES

| Ex. | Rate Oz./100 Lbs. | % Germination |
|---|---|---|
| 3 | 4 | 92 |
| 72 | 2 | 93 |
| 14 | 2 | 92 |
| 11 | 2 | 85 |
| 4 | 2 | 96 |
| 22 | 2 | 90 |
| 23 | 2 | 89 |
| 6 | 4 | 96 |
| 71 | 1 | 97 |
| 73 | 2 | 91 |
| 20 | 2 | 88 |
| 17 | 1 | 92 |
| 18 | 2 | 74 |
| 9 | 2 | 90 |
| 1 | 2 | 88 |
| 44 | 2 | 90 |
| 45 | 4 | 81 |
| 52 | 4 | 49 |
| 57 | 4 | 73 |
| 58 | 4 | 48 |
| 59 | 2 | 60 |
| 8 | 1 | 94 |
| 60 | 2 | 83 |
| 61 | 1 | 77 |
| 62 | 2 | 90 |
| 46 | 1 | 85 |
| 7 | 1 | 93 |
| 29 | 1 | 69 |
| 30 | 1 | 79 |
| 36 | 1 | 73 |
| 37 | 1 | 78 |

Typical untreated control 10–20%

EXAMPLE 85

Foliage spray of dithiin tetroxides for protecting tomato plants from infection by the early blight fungus, *Alternaria solani*.

This Example demonstrates the usefulness of the chemicals of the present invention as foliar fungicides to protect plats from infection by fungi.

One gram of the chemical to be tested was mixed with three ml aceone and 50 mg of a non-ionic surface-active agent (a condensation product of an alkylphenol and ethylene oxide; Triton X-100; trademark). The acetone and surface-active agent are known to be inactive in the biological tests run. The mixture was diluted with water, giving suspensions containing 1000 ppm of the chemical. These suspensions were sprayed on duplicate six-inch tomato plants (variety Clark's Early Special) using a gun-type sprayer which delivered 2.5 ml per second. The plants were then placed in the greenhouse, together with untreated check plants. Twenty-four hours later the treated and untreated check plants were inoculated with a suspension of *Alternaria solani* spores by means of a 20-second spray from an atomizer sprayer (delivery rate 1 ml per second).

The plants were then kept overnight in a control chamber at a temperature of 75° F. and 100% relative humidity. In the morning the plants were transferred to the greenhours. Three days later the disease was scored by comparing the number of disease lesions of the treated plants with the untreated check.

The formula to determine percent control is:

$$1 - \frac{LT}{LU} \times 100 = \% \text{ Control}$$

where LT stands for the average number of lesions on the treated plant and LU stands for the average number of lesions on the untreated plant.

The results are shown in TABLE VII, where the test chemicals bear the Example numbers of TABLE V.

TABLE VII

CONTROL OF TOMATO EARLY BLIGHT DISEASE
BY FOLIAGE APPLICATION OF DITHIIN TETROXIDES

| Ex. | % Control |
|---|---|
| 2 | 75 |
| 11 | 34 |
| 4 | 53 |
| 18 | 81 |
| 6 | 90 |
| 20 | 85 |
| 26 | 86 |
| 44 | 91 |
| 45 | 94 |
| 47 | 96 |
| 53 | 73 |
| 52 | 73 |
| 5 | 98 |
| 50 | 98 |
| 59 | 90 |
| 56 | 98 |
| 60 | 78 |
| 61 | 70 |
| 66 | 93 |
| 36 | 51 |
| 37 | 70 |
| 41 | 97 |
| 43 | 71 |
| 25 | 93 |
| 55 | 96 |

EXAMPLE 86

Antifungal activity of dithiin tetroxides demonstrated by fungicide disc test.

The chemicals of the invention were dissolved in acetone, and applied at 500 ppm to 13 mm antibiotic testing discs by dipping the discs in the test solutions. After drying, the treated discs (4 per plate) were placed on the surface of mycological agar in a Petri plate, then 7 mm plugs of mycelium of various fungi were placed on the center of the discs in such fashion that the fungus mat was in direct contact with the treated disc. The fungitoxic activity of the chemicals was measured by comparing growth (colony radius) of the fungus on the treated discs with that on untreated controls. Colony radius was measured when untreated controls reached 80–90% of the area available for growth on the plates. The fungi tested were *Alternaria solani* (A), *Fusarium oxysporum* (F), *Pythium* sp. (P) and *Rhizoctonia solani* (R). The results are shown in TABLE VIII, expressed as % inhibition.

TABLE VIII

ANTIFUNGAL ACTIVITY OF DITHIIN TETROXIDES
DEMONSTRATED BY FUNGICIDE DISC TEST

| Ex. | A | F | P | R |
|---|---|---|---|---|
| 10 | 50 | 70 | 100 | 85 |
| 12 | 80 | 35 | 30 | 70 |

TABLE VIII-continued

ANTIFUNGAL ACTIVITY OF DITHIIN TETROXIDES
DEMONSTRATED BY FUNGICIDE DISC TEST

| Ex. | A | F | P | R |
|---|---|---|---|---|
| 24 | 0 | 70 | 0 | 60 |
| 13 | 80 | 85 | 95 | 85 |
| 19 | 80 | 90 | 100 | 100 |
| 21 | 75 | 90 | 85 | 85 |
| 79 | 50 | 50 | 100 | 0 |
| 74 | 90 | 95 | 100 | 85 |
| 54 | 85 | 100 | 90 | 95 |
| 65 | 0 | 45 | 85 | 0 |
| 75 | 65 | 80 | 65 | 85 |
| 67 | 90 | 75 | 85 | 70 |
| 35 | 70 | 70 | 25 | 85 |

EXAMPLE 87

Antibacterial activity of dithiin tetroxides demonstrated by trypticase soy broth test.

The chemicals of the invention were dissolved in acetone at a concentration of 3000 ppm. 0.1 ml of this solution, placed in 3 ml trypticase soy broth provided a chemical concentration of 100 ppm for the test.

To each of the test chemical preparations was added a loopful of bacterial suspension of one of the following organisms (age 72 hrs):

*Bacillus subtilis*
*Staphylococcus aureus*
*Pseudomonas aeruginosa*
*Xanthomonas phaseoli*
*Aureobasidium pullulans*

The tubes were incubated at 37° C. for 24 or 48 hours before initial readings were taken. If there was no bacterial growth at 24 or 48 hours the chemical was rated as + (see TABLE VIII) as an antibacterial and a loopful of the treated medium was transferred to an untreated trypticase broth. The tubes were examined after 24 hours to determine whether the chemical exhibited a bactericidal or a bacteristatic effect. The results of these test are given in TABLE IX, wherein * indicates bacteristatic, + indicates bactericidal, and - indicates low activity.

TABLE IX

ANTIBACTERIAL ACTIVITY OF DITHIIN TETROXIDES,
DEMONSTRATED BY THE TRYPTICASE SOY BROTH TEST

| Ex. | Bacillus | Staph | Pseudomonas | Xanthomonas | Pullularia |
|---|---|---|---|---|---|
| 3 | + | + | + | * | − |
| 72 | − | − | − | − | + |
| 2 | + | + | + | + | − |
| 11 | − | − | * | + | − |
| 76 | | * | * | − | − |
| 14 | * | * | * | + | − |
| 18 | − | − | − | + | − |
| 6 | * | * | * | − | + |
| 71 | + | + | + | * | + |
| 73 | * | * | * | + | + |
| 28 | − | − | * | − | − |
| 20 | * | * | − | − | − |
| 9 | * | * | * | * | + |
| 79 | − | − | * | − | − |
| 80 | − | − | − | − | + |
| 82 | − | − | * | − | + |
| 17 | * | * | − | − | + |
| 74 | − | − | − | − | + |
| 24 | − | − | * | − | + |
| 1 | * | + | + | * | + |
| 44 | * | * | + | * | + |
| 47 | * | − | − | − | + |
| 48 | * | * | * | − | + |
| 49 | + | − | * | + | + |
| 53 | * | − | − | − | + |
| 55 | * | * | * | − | + |
| 45 | | | * | + | |
| 52 | − | * | * | − | − |
| 50 | + | + | * | − | − |

TABLE IX-continued

ANTIBACTERIAL ACTIVITY OF DITHIIN TETROXIDES, DEMONSTRATED BY THE TRYPTICASE SOY BROTH TEST

| Ex. | Bacillus | Staph | Pseudo-monas | Xantho-monas | Pullu-laria |
|---|---|---|---|---|---|
| 57 | * | * | − | − | + |
| 58 | * | − | − | − | + |
| 8 | − | * | − | − | − |
| 56 | − | − | − | * | + |
| 60 | * | − | − | − | + |
| 61 | * | * | − | * | + |
| 63 | * | − | − | − | + |
| 64 | − | − | − | − | + |
| 68 | − | − | * | − | − |
| 69 | − | * | * | − | − |
| 70 | − | * | − | − | − |
| 46 | − | − | − | + | + |
| 7 | − | * | * | − | − |
| 66 | * | * | * | − | − |
| 32 | − | − | * | − | − |
| 33 | * | * | * | − | − |
| 77 | − | − | − | + | + |
| 31 | − | * | * | − | − |
| 35 | − | − | * | − | − |
| 78 | − | − | − | − | + |
| 38 | − | − | * | − | − |
| 36 | * | + | * | * | − |
| 40 | * | − | − | − | − |
| 37 | * | * | − | − | − |
| 42 | − | + | − | − | − |

EXAMPLE 88

Inhibition of Southern Bean Mosaic Virus disease by dithiin tetroxides.

The chemicals of the invention were applied to 4–6 day old Pinto bean plants which were previously inoculated with Southern Bean Mosaic Virus. Plants were inoculated by applying a mixture of southern bean mosaic virus extract and silicon carbide abrasive to the primary leaves of bean plants with a glass T-bar inoculator tool. The minute wounds produced by the abrasive allow the virus to enter the plant tissue. Inoculated plants are kept from sunlight for approximately four hours before chemical treatment to allow wound healing. The chemicals were dissolved in acetone (600 mg + 5 mlacetone/100 ml spray solution) or other suitable solvent and then suspended in water by adding a suitable amount (1 drop/100 ml) of a surfactant such as Triton X-100. The suspended chemicals were then sprayed on the plants to the point of runoff at a pressure of 20 psi. After 4–6 days local lesions produced by the virus appeared on untreated leaves. The effectiveness of the chemical treatment, as shown in TABLE X, was determined by the following formula:

$$\% \text{ Control} = 1 - \frac{LT}{LC} \times 100$$

where LT stands for the average lesion count in the treatment and LC stands for the average lesion count in the control.

TABLE X

INHIBITION OF SOUTHERN BEAN MOSAIC VIRUS DISEASE BY DITHIIN TETROXIDES
% Control

| Ex. | 6000 | 3000 PPM |
|---|---|---|
| 72 | 65 | — |
| 16 | 80 | — |
| 15 | 90 | 55 |
| 80 | 75 | — |
| 14 | 70 | 56 |
| 27 | — | 100 |
| 73 | 70 | 71 |
| 28 | 100 | — |
| 13 | 80 | — |
| 19 | 75 | — |
| 83 | 75 | — |
| 32 | 60 | — |
| 33 | 70 | 59 |
| 77 | 85 | 53 |
| 34 | 70 | 70 |
| 78 | 90 | — |
| 38 | — | 75 |
| 41 | 70 | 93 |

EXAMPLE 89

Control of soybean seedling disease by seed treatment with dithiin tetroxides.

Chemicals of the invention were applied to 50 gram seed lots of soybean seeds (Variety Corsoy) by tumbling the seed lots with 31 mg of chemical plus an equal amount of dixie clay carrier for dispersal. This is an application rate of 1 ounce of active ingredient per 100 pounds of seed.

Seeds were planted in flats of soil, which were naturally infested with disease producing organisms. Eight replications of each planting, 25 seeds per row, were made with one replication of each treatment in a given flat. After planting, each flat of soil was wetted with a measured amount of water (1 liter), then placed in a controlled temperature chamber (55° F.) for ten days to promote disease development.

Flats were then transferred to a normal greenhouse environment (75° F.) where the seeds continued germination and growth for one week. At this time the seedlings were counted and the value of the chemical protectant was assessed on the basis of the percentage germination compared to the untreated control, with the results shown in TABLE XI. The formula for this determination was as follows:

$$\% \text{ Germination} = \frac{E}{P} \times 100$$

where E stands for the number of emerged seedlings and P stands for the number of seeds planted.

TABLE XI

CONTROL OF SOYBEAN SEELING DISEASE BY SEED TREATMENT WITH DITHIIN TETROXIDES

| Ex. | % Germination |
|---|---|
| 3 | 80 |
| 9 | 77 |
| 14 | 94 |
| 6 | 93 |
| 71 | 86 |
| 17 | 75 |
| 22 | 63 |
| 20 | 92 |
| 1 | 95 |
| 8 | 90 |
| 7 | 94 |

Typical Untreated Control 30

Typical Untreated Control 30

We claim:

1. A method of controlling fungi or bacteria comprising applying to a locus, subject to attack by fungi or bacteria, in bactericidally or fungicidally effective amount, a 2,3-dihydro-1,4-dithiin 1,1,4,4-tetroxide having the following structural formula:

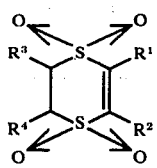

wherein $R_1$, $R_2$, $R_3$, and $R_4$ are independently hydrogen, alkyl having 1 to 14 carbon atoms, aryl, aryl substituted with one to three substituents selected from the group consisting of lower alkyl, halogen, lower alkoxy, nitro, and aryl, alkoxymethyl wherein the alkyl group contains 1 to 8 carbon atoms, aryloxymethyl, alkylaminomethyl wherein the alkyl group contains 1 to 8 carbon atoms, or adjacent R's may be joined together as a chain of 3 to 4 methylene groups.

2. A method as in claim 1 wherein the R's have sets of values selected from the following:

| $R_1$ | $R_2$ | $R_3$ | $R_4$ |
|---|---|---|---|
| H | H | H | H |
| $CH_3$ | H | H | H |
| $CH_3$ | H | $CH_3$ | H |
| $CH_3$ | H | H | $CH_3$ |
| $CH_3$ | $CH_3$ | $nC_6H_{13}$ | H |
| $CH_3$ | H | $C_2H_5$ | H |
| $CH_3$ | H | H | $C_2H_5$ |
| $CH_3$ | $CH_3$ | $nC_8H_{17}$ | H |
| $CH_3$ | H | $C_6H_5$ | H |
| $CH_3$ | H | H | $C_6H_5$ |
| $CH_3$ | H | $nC_8H_{17}$ | H |
| $CH_3$ | H | H | $nC_8H_{17}$ |
| $CH_3$ | H | $CH_3$ | $CH_3$ |
| $CH_3$ | $CH_3$ | $CH_3$ | $CH_3$ |
| $C_2H_5$ | H | H | H |
| $C_2H_5$ | H | $CH_3$ | H |
| $C_2H_5$ | H | H | $CH_3$ |
| $C_2H_5$ | H | $C_2H_5$ | H |
| $C_2H_5$ | H | H | $C_2H_5$ |
| $C_2H_5$ | H | $nC_4H_9$ | H |
| $C_2H_5$ | H | H | $nC_4H_9$ |
| $C_2H_5$ | H | $CH_3$ | $CH_3$ |
| $C_2H_5$ | H | $nC_6H_{13}$ | H |
| $C_2H_5$ | H | H | $nC_6H_{13}$ |
| $nC_3H_7$ | H | H | H |
| $tC_4H_9$ | H | H | H |
| $nC_5H_{11}$ | H | H | H |
| $(CH_3)_2CHCH_2CH_2$ | H | H | H |
| $C_2H_5$ | $CH_3$ | H | H |
| $C_2H_5$ | $CH_3$ | $CH_3$ | H |
| $C_2H_5$ | $CH_3$ | H | $CH_3$ |
| $-(CH_2)_3-$ | | H | H |
| $-(CH_2)_3-$ | | $CH_3$ | H |
| $-(CH_2)_4-$ | | $CH_3$ | $CH_3$ |
| $-(CH_2)_4-$ | | $-(CH_2)_4-$ | |
| $-(CH_2)_4-$ | | $nC_4H_9$ | H |
| $-(CH_2)_4-$ | | $C_2H_5$ | H |
| $-(CH_2)_4-$ | | $nC_6H_{13}$ | H |
| $CH_3$ | H | $-(CH_2)_4-$ | |
| $C_2H_5$ | H | $-(CH_2)_4-$ | |
| $CH_3$ | $CH_3$ | $-(CH_2)_4-$ | |
| $C_6H_5$ | H | $-(CH_2)_4-$ | |
| $pCH_3OC_6H_4$ | H | $-(CH_2)_4-$ | |
| $pFC_6H_4$ | H | $-(CH_2)_4-$ | |
| $pNO_2C_6H_4$ | H | $-(CH_2)_4-$ | |
| 2naphthyl | H | $-(CH_2)_4-$ | |
| $C_6H_5$ | H | H | H |
| $C_6H_5$ | H | $CH_3$ | H |
| $C_6H_5$ | H | H | $CH_3$ |
| $C_6H_5$ | H | $C_2H_5$ | H |
| $C_6H_5$ | H | H | $C_2H_5$ |
| $C_6H_5$ | H | $CH_3$ | $CH_3$ |
| $pCH_3C_6H_4$ | H | H | H |
| $pCH_3C_6H_4$ | H | $CH_3$ | H |
| $pCH_3C_6H_4$ | H | H | $CH_3$ |
| $pCH_3C_6H_4$ | H | $C_2H_5$ | H |
| $pCH_3C_6H_4$ | H | H | $C_2H_5$ |
| $pC_2H_5C_6H_4$ | H | H | H |
| $pC_2H_5C_6H_4$ | H | $CH_3$ | H |
| $pC_2H_5C_6H_4$ | H | H | $CH_3$ |
| 2,4xylyl | H | H | H |
| 2,5xylyl | H | H | H |
| $pCH_3OC_6H_4$ | H | $CH_3$ | H |
| $pCH_3OC_6H_4$ | H | H | $CH_3$ |
| $pCH_3OC_6H_4$ | H | $C_2H_5$ | H |
| $pCH_3OC_6H_4$ | H | H | $C_2H_5$ |
| $pBrC_6H_4$ | H | H | H |
| $pClC_6H_4$ | H | H | H |
| $pClC_6H_4$ | H | $CH_3$ | H |
| $pClC_6H_4$ | H | H | $CH_3$ |
| $pClC_6H_4$ | H | $C_2H_5$ | H |
| $pClC_6H_4$ | H | H | $C_2H_5$ |
| $pClC_6H_4$ | H | $CH_3$ | $CH_3$ |
| $pFC_6H_4$ | H | H | H |
| $pFC_6H_4$ | H | $CH_3$ | H |
| $pFC_6H_4$ | H | H | $CH_3$ |
| $pFC_6H_4$ | H | $C_2H_5$ | H |
| $pFC_6H_4$ | H | H | $C_2H_5$ |
| $pNO_2C_6H_4$ | H | H | H |
| $pNO_2C_6H_4$ | H | $CH_3$ | H |
| $pNO_2C_6H_4$ | H | H | $CH_3$ |
| $pC_6H_5C_6H_4$ | H | H | H |
| 2naphthyl | H | $CH_3$ | H |
| 2naphthyl | H | H | $CH_3$ |
| 2naphthyl | H | $C_2H_5$ | H |
| 2naphthyl | H | H | $C_2H_5$ |
| $C_6H_5$ | $nC_4H_9$ | H | H |
| $C_6H_5$ | $nC_4H_9$ | $CH_3$ | H |
| $C_6H_5$ | $nC_4H_9$ | H | $CH_3$ |
| $C_6H_5$ | $C_6H_5$ | $C_2H_5$ | H |
| $CH_3$ | H | $CH_3OCH_2$ | H |
| $CH_3$ | H | H | $CH_3OCH_2$ |
| $CH_3$ | H | $(CH_3)_2CHOCH_2$ | H |
| $CH_3$ | H | H | $(CH_3)_2CHOCH_2$ |
| $CH_3$ | H | $nC_4H_9OCH_2$ | H |
| $CH_3$ | H | H | $nC_4H_9OCH_2$ |
| $CH_3$ | $CH_3$ | $C_2H_5OCH_2$ | H |
| $CH_3$ | $CH_3$ | $(CH_3)_2CHOCH_2$ | H |
| $CH_3$ | $CH_3$ | $nC_4H_9OCH_2$ | H |
| $CH_3$ | $CH_3$ | $C_6H_5OCH_2$ | H |
| $C_2H_5$ | H | $nC_4H_9OCH_2$ | H |
| $C_2H_5$ | H | H | $nC_4H_9OCH_2$ |
| $C_6H_5$ | H | $CH_3OCH_2$ | H |
| $C_6H_5$ | H | H | $CH_3OCH_2$ |
| $C_6H_5$ | H | $nC_4H_9OCH_2$ | H |
| $C_6H_5$ | H | H | $nC_4H_9OCH_2$ |
| $-(CH_2)_4-$ | | $(CH_3)_2CHOCH_2$ | H |
| $-(CH_2)_4-$ | | $nC_4H_9OCH_2$ | H |
| $CH_3$ | $CH_3$ | $(C_2H_5)_2NCH_2$ | H |
| 2-napthyl | H | H | H |

3. A method as in claim 1, wherein the R's have sets of values selected from the following:

| $R_1$ | $R_2$ | $R_3$ | $R_4$ |
|---|---|---|---|
| $CH_3$ | H | $C_6H_5$ | H |
| $CH_3$ | H | H | $C_6H_5$ |
| $CH_3$ | H | $CH_3$ | $CH_3$ |
| $C_2H_5$ | H | $CH_3$ | $CH_3$ |
| $C_2H_5$ | $CH_3$ | H | H |
| $-(CH_2)_4-$ | | $nC_4H_9$ | H |
| $CH_3$ | H | $-(CH_2)_4-$ | |
| $pFC_6H_4$ | H | $-(CH_2)_4-$ | |
| $C_6H_5$ | H | H | H |
| $C_6H_5$ | H | $CH_3$ | H |
| $C_6H_5$ | H | H | $CH_3$ |
| $pCH_3C_6H_4$ | H | $CH_3$ | H |

-continued

| $R_1$ | $R_2$ | $R_3$ | $R_4$ |
|---|---|---|---|
| $pCH_3C_6H_4$ | H | H | $CH_3$ |
| $pC_2H_5C_6H_4$ | H | H | H |
| $pC_2H_5C_6H_4$ | H | H | $CH_3$ |
| $pC_2H_5C_6H_4$ | H | $CH_3$ | H |
| $pCH_3OC_6H_4$ | H | $CH_3$ | H |
| $pCH_3OC_6H_4$ | H | H | $CH_3$ |
| $pClC_6H_4$ | H | $C_2H_5$ | H |
| $pClC_6H_4$ | H | H | $C_2H_5$ |
| $pFC_6H_4$ | H | $CH_3$ | H |
| $pFC_6H_4$ | H | H | $CH_3$ |
| $pFC_6H_4$ | H | $C_2H_5$ | H |
| $pFC_6H_4$ | H | H | $C_2H_5$ |
| $CH_3$ | H | $CH_3OCH_2$ | H |
| $CH_3$ | H | H | $CH_3OCH_2$ |
| $CH_3$ | H | $nC_4H_9OCH_2$ | H |
| $CH_3$ | H | H | $nC_4H_9OCH_2$ |
| $C_6H_5$ | H | $CH_3OCH_2$ | H |
| $C_6H_5$ | H | H | $CH_3OCH_2$ |
| —$(CH_2)_4$— | | $nC_4H_9OCH_2$ | H |

4. A method as in claim 1, wherein the R's have sets of values selected from the following:

| $R_1$ | $R_2$ | $R_3$ | $R_4$ |
|---|---|---|---|
| $CH_3$ | H | $C_6H_5$ | H |
| $CH_3$ | H | H | $C_6H_5$ |
| —$(CH_2)_4$— | | $nC_4H_9$ | H |
| $CH_3$ | H | —$(CH_2)_4$— | |
| $pFC_6H_4$ | H | —$(CH_2)_4$— | |
| $C_6H_5$ | H | $CH_3$ | H |
| $C_6H_5$ | H | H | $CH_3$ |
| $pCH_3C_6H_4$ | H | $CH_3$ | H |
| $pCH_3C_6H_4$ | H | H | $CH_3$ |
| $pC_2H_5C_6H_4$ | H | H | H |
| $pC_2H_5C_6H_4$ | H | $CH_3$ | H |
| $pC_2H_5C_6H_4$ | H | H | $CH_3$ |
| $pCH_3OC_6H_4$ | H | $CH_3$ | H |
| $pCH_3OC_6H_4$ | H | H | $CH_3$ |
| $p$-$ClC_6H_4$ | H | $C_2H_5$ | H |
| $p$-$ClC_6H_4$ | H | H | $C_2H_5$ |
| $pFC_6H_4$ | H | $CH_3$ | H |
| $pFC_6H_4$ | H | H | $CH_3$ |
| $pFC_6H_4$ | H | $C_2H_5$ | H |
| $pFC_6H_4$ | H | H | $C_2H_5$ |
| $CH_3$ | H | $CH_3OCH_2$ | H |
| $CH_3$ | H | H | $CH_3OCH_2$ |
| $CH_3$ | H | $nC_4H_9OCH_2$ | H |
| $CH_3$ | H | H | $nC_4H_9OCH_2$ |
| $C_6H_5$ | H | $CH_3OCH_2$ | H |
| $C_6H_5$ | H | H | $CH_3OCH_2$ |
| —$(CH_2)_4$— | | $nC_4H_9OCH_2$ | H |

5. A method as in claim 1, wherein the R's have sets of values selected from the following:

| $R_1$ | $R_2$ | $R_3$ | $R_4$ |
|---|---|---|---|
| $C_6H_5$ | H | H | H |
| $C_2H_5$ | $CH_3$ | H | H |
| $CH_3$ | H | $CH_3$ | $CH_3$ |
| $pC_2H_5C_6H_4$ | H | H | H |
| $CH_3$ | H | $C_6H_5$ | H |
| $CH_3$ | H | H | $C_6H_5$ |
| $C_6H_5$ | H | $CH_3OCH_2$ | H |
| $C_6H_5$ | H | H | $CH_3OCH_2$ |
| $pClC_6H_4$ | H | $CH_2CH_3$ | H |
| $pClC_6H_4$ | H | H | $CH_2CH_3$ |
| $pFC_6H_4$ | H | —$(CH_2)_4$— | |

6. A method of controlling fungi or bacteria on plant life comprising applying to the plant life, in amount effective to control the fungi or bacteria on plant life, a 2,3-dihydro-1,4-dithiin 1,1,4,4-tetroxide selected from the group consisting of 2,3-dihydro-5-phenyl-1,4-dithiin 1,1,4,4-tetroxide, 2-ethyl-5,6-dihydro-3-methyl-1,4-dithiin 1,1,4,4-tetroxide, 2,3-dihydro-2,3,5-trimethyl-1,4-dithiin 1,1,4,4-tetroxide, 2-(4-ethylphenyl)-5,6-dihydro-1,4-dithinn 1,1,4,4-tetroxide, 2,3-dihydro-5-methyl-3-phenyl-1,4-dithiin 1,1,4,4-tetroxide, 2,3-dihydro-5-methyl-2-phenyl-1,4-dithiin 1,1,4,4-tetroxide, 2,3-dihydro-2-methoxymethyl-5-phenyl-1,4-dithiin 1,1,4,4-tetroxide, 2,3-dihydro-2-methoxymethyl-6-phenyl-1,4-dithiin 1,1,4,4-tetroxide, 2-(4-chlorophenyl)-5-ethyl-5,6-dihydro-1,4-dithiin 1,1,4,4-tetroxide, 2-(4-chlorophenyl)-6-ethyl-5,6-dihydro-1,4-dithiin 1,1,4,4-tetroxide, and 2-(4-fluorophenyl)-4a, 5, 6, 7, 8, 8a-hexahydro-1,4-benzodithiin 1,1,4,4-tetroxide.

7. A method of controlling fungi comprising applying to a locus subject to attach by fungi, in amount effective to control the fungi, a 2,3-dihydro-1,4-dithiin 1,1,4,4-tetroxide selected from the group consisting of 2,3-dihydro-5-phenyl-1,4-dithiin 1,1,4,4-tetroxide, 2-(4-ethylphenyl)-5,6-dihydro-1,4-dithiin 1,1,4,4-tetroxide, 2,3-dihydro-5-methyl-3-phenyl-1,4-dithiin 1,1,4,4-tetroxide, 2,3-dihydro-5-methyl-2-phenyl-1,4-dithiin 1,1,4,4-tetroxide, 2,3-dihydro-2, 3,5-trimethyl-1,4-dithinn 1,1,4,4-tetroxide, 2,3-dihydro-2-methoxymethyl-5-phenyl-1,4-dithiin 1,1,4,4-tetroxide, 2,3-dihydro-2-methoxymethyl-6-phenyl-1,4-dithiin 1,1,4,4-tetroxide, 2-(4-chlorophenyl)-5-ethyl-5,6-dihydro-1,4-dithiin 1,1,4,4-tetroxide and 2-(4-chlorophenyl)-6-ethyl-5,6-dihydro-1,4-dithiin 1,1,4,4-tetroxide.

8. A method as in claim 7 in which the said locus to which the 2,3-dihydro-1,4-dithiin 1,1,4,4-tetroxide is applied is plant life.

9. A method as in claim 8 in which the said 2,3-dihydro-1,4-dithiin 1,1,4,4-tetroxide is 2,3-dihydro-5-phenyl-1,4-dithiin 1,1,4,4-tetroxide.

10. A method as in claim 8 in which the said 2,3-dihydro-1,4-dithiin 1,1,4,4-tetroxide is 2-(4-ethylphenyl)-5,6-dihydro-1,4-dithiin 1,1,4,4-tetroxide.

11. A method as in claim 8 in which the said 2,3-dihydro-1,4-dithiin 1,1,4,4-tetroxide is 2,3-dihydro-5-methyl-3-phenyl-1,4-dithiin 1,1,4,4-tetroxide.

12. A method as in claim 8 in which the said 2,3-dihydro-1,4-dithiin 1,1,4,4-tetroxide is 2,3-dihydro-5-methyl-2-phenyl-1,4-dithiin 1,1,4,4-tetroxide.

13. A method as in claim 8 in which the said 2,3-dihydro-1,4-dithiin 1,1,4,4-tetroxide is 2,3-dihydro-2,3,5-trimethyl-1,4-dithiin 1,1,4,4-tetroxide.

14. A method as in claim 8 in which the said 2,3-dihydro-1,4-dithiin 1,1,4,4-tetroxide is 2,3-dihydro-2-methoxymethyl-5-phenyl-1,4-dithiin 1,1,4,4-tetroxide.

15. A method as in claim 8 in which the said 2,3-dihydro-1,4-dithiin 1,1,4,4-tetroxide is 2,3-dihydro-2-methoxymethyl-6-phenyl-1,4-dithiin 1,1,4,4-tetroxide.

16. A method as in claim 8 in which the said 2,3-dihydro-1,4-dithiin 1,1,4,4-tetroxide is 2-(4-chlorophenyl)-5-ethyl-5,6-dihydro-1,4-dithiin 1,1,4,4-tetroxide.

17. A method as in claim 8 in which the said 2,3-dihydro-1,4-dithiin 1,1,4,4-tetroxide is 2-(4-chlorophenyl)-6-ethyl-5,6-dihydro-1,4-dithiin 1,1,4,4-tetroxide.

18. A method of controlling bacteria comprising applying to a locus subject to attack by bacteria, in amount effective to control the bacteria, a 2,3-dihydro-1,4-dithiin 1,1,4,4-tetroxide selected from the group consisting of 2,3-dihydro-5-phenyl-1,4-dithiin 1,1,4,4-tetroxide, 2,3-dihydro-2,3,5,trimethyl-1,4-dithiin 1,1,4,4-tetroxide, 2,3-dihydro-5-methyl-3-phenyl-1,4-dithiin 1,1,4,4-tetroxide and 2,3-dihydro-5-methyl-2-phenyl-1,4-dithiin 1,1,4,4-tetroxide.

19. A method as in claim 18 in which the said locus to which the 2,3-dihydro-1,4-dithiin 1,1,4,4-tetroxide is applied is plant life.

20. A method as in claim 19 in which the said 2,3-dihydro-1,4-dithiin 1,1,4,4-tetroxide is 2,3-dihydro-5-phenyl-1,4-dithiin 1,1,4,4-tetroxide.

21. A method as in claim 19 in which the said 2,3-dihydro-1,4-dithiin 1,1,4,4-tetroxide is 2,3-dihydro-2,3,5-trimethyl-1,4-dithiin 1,1,4,4-tetroxide.

22. A method as in claim 19 in which the said 2,3-dihydro-1,4-dithiin 1,1,4,4-tetroxide is 2,3-dihydro-5-methyl-3-phenyl-1,4-dithiin 1,1,4,4-tetroxide.

23. A method as in claim 19 in which the said 2,3-dihydro-1,4-dithiin 1,1,4,4-tetroxide is 2,3-dihydro-5-methyl-2-phenyl-1,4-dithiin 1,1,4,4-tetroxide.

24. A method of controlling fungi comprising applying 2-(or 3-)ethyl-2,3-dihydro-5-phenyl-1,4-dithiin 1,1,4,4-tetroxide to a locus subject to attack by fungi, in amount effective to control the fungi.

25. A method of controlling bacteria comprising applying 2,3-dihydro-5-methyl-1,4-dithiin 1,1,4,4-tetroxide to a locus subject to attack by bacteria, in amount effective to control the bacteria.

26. A 2,3-dihydro-1,4-dithiin 1,1,4,4-tetroxide of the formula:

$$\begin{array}{c} O \diagdown \diagup O \\ R^3 - S - R^1 \\ | \quad | \\ R^4 - S - R^2 \\ O \diagup \diagdown O \end{array}$$

wherein the R's have sets of values as follows:

| $R_1$ | $R_2$ | $R_3$ | $R_4$ |
|---|---|---|---|
| $pC_2H_5C_6H_4$ | H | H | H |
| $CH_3$ | H | $C_6H_5$ | H |
| $CH_3$ | H | H | $C_6H_5$ |
| $C_6H_5$ | H | $CH_3OCH_2$ | H |
| $C_6H_5$ | H | H | $CH_3OCH_2$ |
| $pClC_6H_4$ | H | $CH_2CH_3$ | H |
| $pClC_6H_4$ | H | H | $CH_2CH_3$ |
| $pFC_6H_4$ | H | $-(CH_2)_4-$ | |

27. A chemical as in claim 26 which is 2,3-dihydro-5-methyl-3-phenyl-1,4-dithiin 1,1,4,4-tetroxide.

28. A chemical as in claim 26 which is 2,3-dihydro-5-methyl-2-phenyl-1,4-dithiin 1,1,4,4-tetroxide.

29. A chemical as in claim 26 which is 2,3-dihydro-2-methoxymethyl-5-phenyl-1,4-dithiin 1,1,4,4-tetroxide.

30. A chemical as in claim 26 which is 2,3-dihydro-2-methoxymethyl-6-phenyl-1,4-dithiin 1,1,4,4-tetroxide.

31. A chemical as in claim 26 which is 2-(4-chlorophenyl)-5-ethyl-5,6-dihydro-1,4-dithiin 1,1,4,4-tetroxide.

32. A chemical as in claim 26 which is 2-(4-chlorophenyl)-6-ethyl-5,6-dihydro-1,4-dithiin 1,1,4,4-tetroxide.

33. A chemical as in claim 26 which is 2-(4-fluorophenyl)-4a,5,6,7,8,8a-hexahydro-1,4-benzodithiin 1,1,4,4-tetroxide.

34. A chemical as in claim 26 which is 2-(4-ethylphenyl)-5,6-dihydro-1,4-dithiin 1,1,4,4-tetroxide.

35. 2-(or 3-)Ethyl-2,3-dihydro-5-phenyl-1,4-dithiin 1,1,4,4-tetroxide.

* * * * *